United States Patent
Hakes et al.

(10) Patent No.: US 9,238,491 B1
(45) Date of Patent: Jan. 19, 2016

(54) CRAWLER SHOE HAVING WEAR MEASUREMENT FEATURES

(71) Applicant: Caterpillar Inc., Peoria, IL (US)

(72) Inventors: David J. Hakes, Brimfield, IL (US); Roger E. Lawson, Brimfield, IL (US); Thomas E. Oertley, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 14/338,120

(22) Filed: Jul. 22, 2014

(51) Int. Cl.
*G01M 13/00* (2006.01)
*B62D 55/20* (2006.01)
*G07C 5/08* (2006.01)
*B62D 55/06* (2006.01)

(52) U.S. Cl.
CPC .......... *B62D 55/20* (2013.01); *B62D 55/06* (2013.01); *G07C 5/085* (2013.01)

(58) Field of Classification Search
None
See application file for complete search history.

(56) References Cited

U.S. PATENT DOCUMENTS

| | | | |
|---|---|---|---|
| 5,348,515 A | 9/1994 | Miller | |
| 6,041,529 A | 3/2000 | Ruvang | |
| 6,176,127 B1* | 1/2001 | Kim | G01B 7/048 73/146 |
| 2003/0034690 A1 | 2/2003 | Hori et al. | |
| 2004/0112116 A1* | 6/2004 | Dunning | B23Q 3/1543 73/7 |
| 2008/0072673 A1* | 3/2008 | Carnevale | G01B 17/02 73/602 |
| 2008/0157588 A1* | 7/2008 | Lyasko | B62D 55/28 305/201 |
| 2013/0255354 A1* | 10/2013 | Hawkins | G01N 3/56 73/7 |
| 2014/0139332 A1* | 5/2014 | Mouchet | B60C 23/0479 340/442 |
| 2014/0324301 A1* | 10/2014 | Rebinsky | E02F 9/267 701/50 |
| 2015/0066291 A1* | 3/2015 | Johannsen | B62D 55/32 701/34.4 |
| 2015/0081166 A1* | 3/2015 | Diekevers | E62D 55/14 701/34.4 |
| 2015/0101391 A1* | 4/2015 | Kita | G01N 3/56 73/7 |
| 2015/0233786 A1* | 8/2015 | Pieper | G01M 13/00 702/34 |

FOREIGN PATENT DOCUMENTS

GB 2482516 2/2012

OTHER PUBLICATIONS

U.S. Appl. No. 14/181,313, filed Feb. 14, 2014, Caterpillar Inc.
Ruffe, H. Introducing Modustri (by Agent X), Aug. 22, 2013, 9 pages.
Wasson, C., Staying Out of the Shop, Dec. 31, 2009, 3 pages.

* cited by examiner

*Primary Examiner* — Jonathan M Dager
(74) *Attorney, Agent, or Firm* — Finnegan, Henderson, Farabow, Garrett & Dunner, LLP (57) ABSTRACT

A crawler shoe for a mining vehicle includes a first wear surface, a second wear surface positioned opposite the first wear surface, a recess formed within the first wear surface and including a measurement datum formed at a bottom portion of the recess, wherein the measurement datum is positioned below the first wear surface such that the measurement datum is subjected to less service wear than the first wear surface, and an approximately linear transmission path configured to receive an ultrasonic signal and extending from the measurement datum to the second wear surface.

20 Claims, 7 Drawing Sheets

CRAWLER SHOE HAVING WEAR MEASUREMENT FEATURES

CROSS-REFERENCE TO RELATED APPLICATIONS

This application hereby incorporates by reference in its entirety U.S. patent application Ser. No. 14/181,313, filed on Feb. 14, 2014, including the specification, drawings, claims and abstract.

TECHNICAL FIELD

This disclosure relates to a track for a track-driven industrial vehicle, and particularly to a crawler shoe having a feature for determining a wear measurement of the crawler shoe.

BACKGROUND

This section is intended to provide a background or context to the invention recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Large industrial vehicles (e.g., mining shovels) may include an undercarriage or other framework for supporting the vehicle and enabling movement of the vehicle about a work site. The undercarriage may include a track having a series of segments, or crawler shoes, that are pivotally connected and driven about a frame to propel the vehicle. As the undercarriage is operated (e.g., the track is driven about the frame), components of the undercarriage, including the crawler shoes, may become worn due to inherent friction between the undercarriage components, the weight of the vehicle, climatic conditions, and the varied terrain, among other factors. Further, various components of the undercarriage may be "dry-running," or operated without oil or grease lubrication. The crawler shoes for instance, may be configured to interface with load rollers of the undercarriage, and thus may be particularly subject to wear. The undercarriage components may thus require frequent inspection, repair, and/or replacement to maintain efficient operation of the vehicle.

Ultrasonic measurement devices may be used to measure or estimate the wear of the crawler shoes and other undercarriage components. For instance, an ultrasonic measurement device may be configured to send an ultrasonic signal (e.g., a high frequency sound wave) from a first surface of the crawler shoe in the direction of a second opposite surface. The ultrasonic measurement device may then measure the elapsed time before the signal is reflected from the second surface and received at the device in order to determine a thickness of the crawler shoe. However, the crawler shoe may have multiple wear surfaces, such that the wear of a particular surface may not be determinable based on the thickness of the crawler shoe. Also, the wear may occur unevenly across the surface of the shoe, such that the thickness measurement may be different depending on the location of the measurement. Further, some surfaces of the crawler shoe may be rounded or uneven. Thus, an accurate measurement or estimate of the wear of a conventional crawler shoe may be difficult or, under certain circumstances, impossible to obtain using the ultrasonic measurement device or a mechanical measurement device.

SUMMARY

An embodiment of the present disclosure relates to a crawler shoe for a mining vehicle. The crawler shoe includes a first wear surface, a second wear surface positioned opposite the first wear surface, a recess formed within the first wear surface and including a measurement datum formed at a bottom portion of the recess, wherein the measurement datum is positioned below the first wear surface such that the measurement datum is subjected to less service wear than the first wear surface, and an approximately linear transmission path configured to receive an ultrasonic signal and extending from the measurement datum to the second wear surface.

Another embodiment of the present disclosure relates to an undercarriage system. The undercarriage system includes a load roller and a track. The track includes a plurality of interconnected crawler shoes configured to engage the load roller, wherein each of the crawler shoes is pivotably coupled to adjacent crawler shoes by a pin. At least one of the crawler shoes includes a first wear surface, a second wear surface positioned opposite the first wear surface, wherein the second wear surface is configured to engage the load roller, a recess formed within the first wear surface and having a measurement datum formed at a bottom portion of the recess, wherein the measurement datum is positioned below the first wear surface such that the measurement datum is subjected to less service wear than the first wear surface, and an approximately linear transmission path configured to receive an ultrasonic signal and extending from the measurement datum to the second wear surface.

Another embodiment of the present disclosure relates to a computer-implemented method for determining wear of a crawler shoe. The method includes causing a probe of a measurement device to generate and send an ultrasonic signal through an approximately linear transmission path of a crawler shoe, wherein the crawler shoe includes a first wear surface, a second wear surface positioned opposite the first wear surface and configured to reflect the ultrasonic signal, and a recess formed within the first wear surface and including a measurement datum formed at a bottom portion of the recess. The measurement datum is positioned below the first wear surface such that the measurement datum is subjected to less service wear than the first wear surface, and the transmission path extends from the measurement datum to the second wear surface. The method also includes determining a wear measurement of the second wear surface based upon receipt of the ultrasonic signal at the probe.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
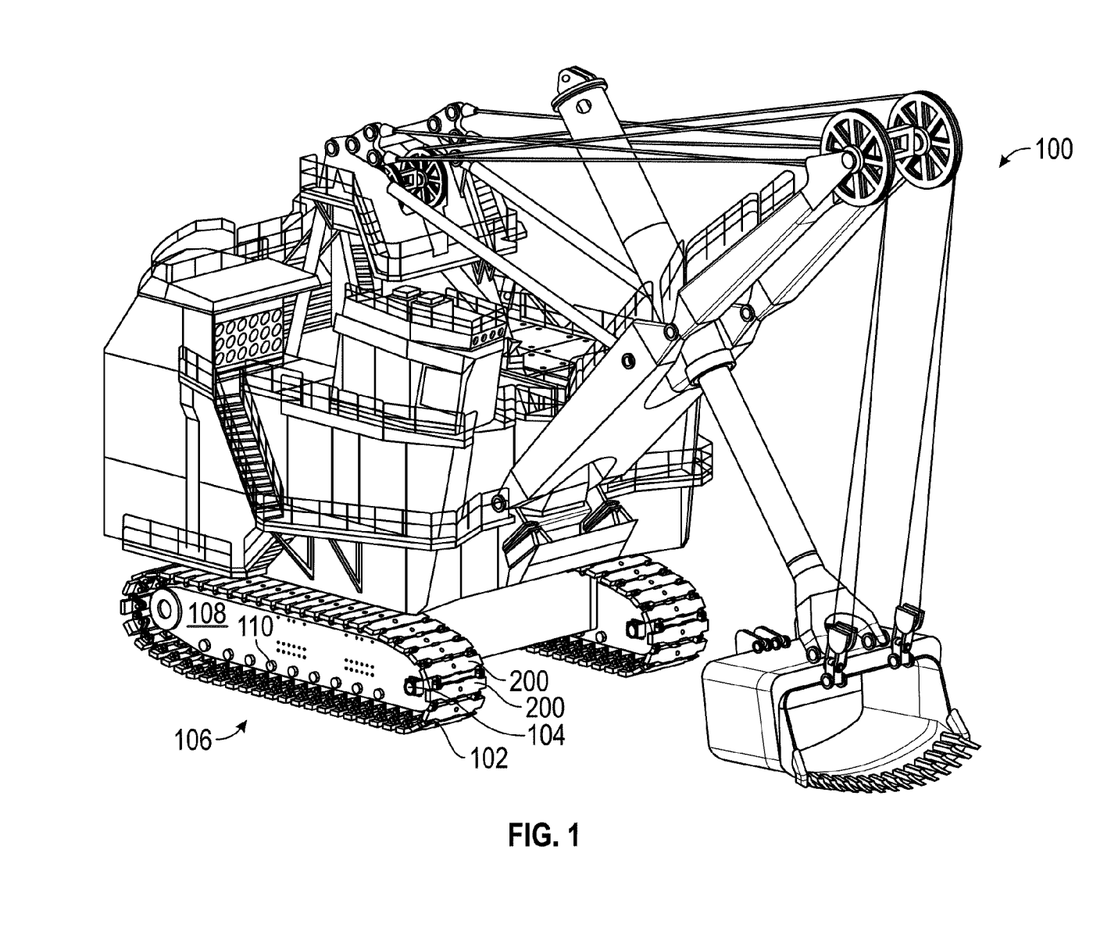
FIG. 1 is a perspective view of a track-driven mining vehicle, according to an exemplary embodiment.

Referring to FIG. 1, a track-driven mining vehicle 100 is shown, according to an exemplary embodiment. The vehicle 100 includes an undercarriage 106 having a continuous and flexible crawler track 102 which rotates about a side frame 108. The crawler track 102 is driven across idler wheel 104 of the undercarriage 106 to propel the vehicle 100 across a ground surface. The crawler track 102 is formed by a series of pivotally coupled crawler shoes 200 (e.g., segments), which are shown in further detail in FIGS. 2 through 6. The crawler shoes 200 combine to form the rounded crawler track 102 configured to traverse mining surfaces, including uneven terrain.

Figure 2:
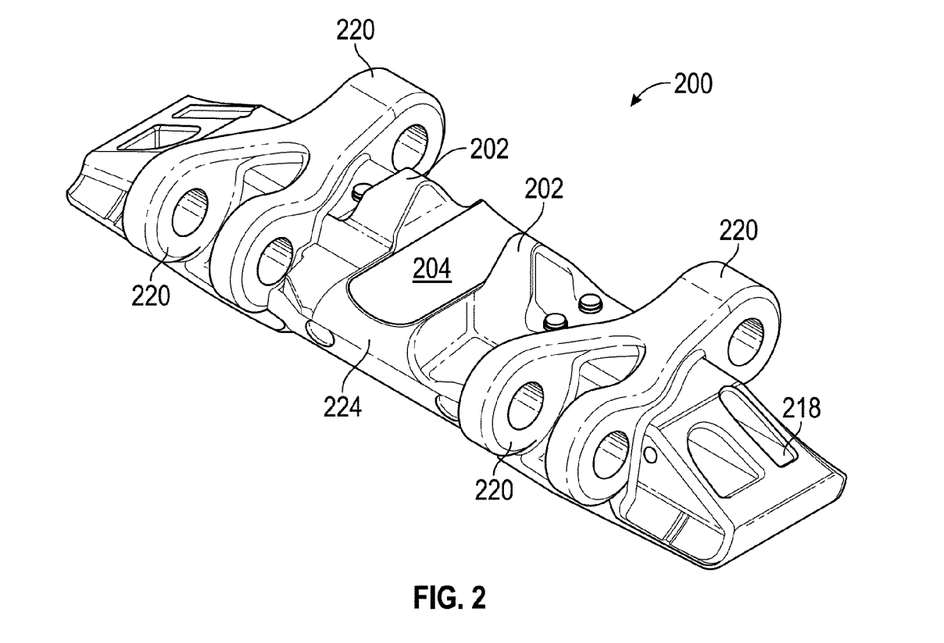
FIG. 2 is a perspective view of a crawler shoe for a mining vehicle track, according to an exemplary embodiment.
Figure 3:
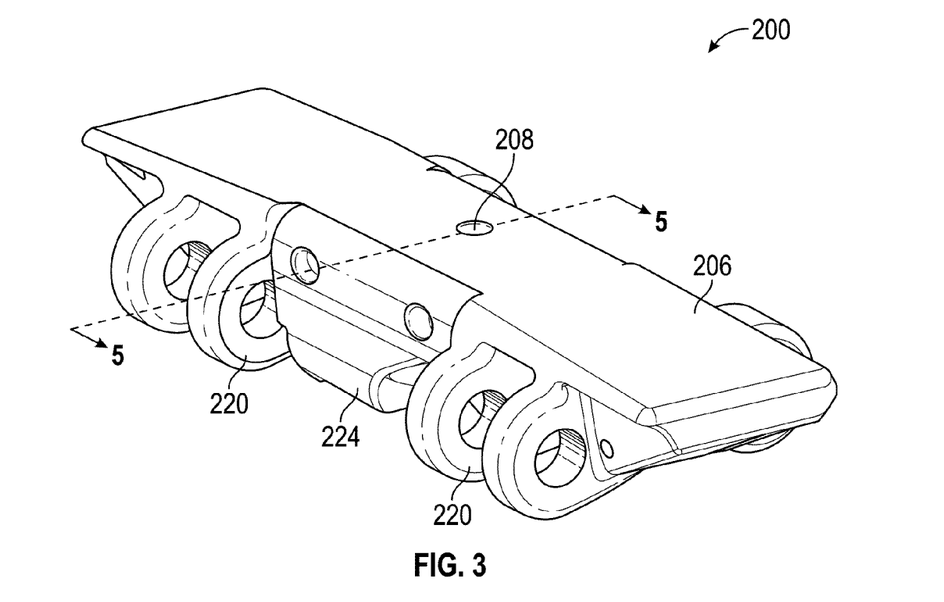
FIG. 3 is another perspective view of the crawler shoe, according to an exemplary embodiment.
Figure 4:
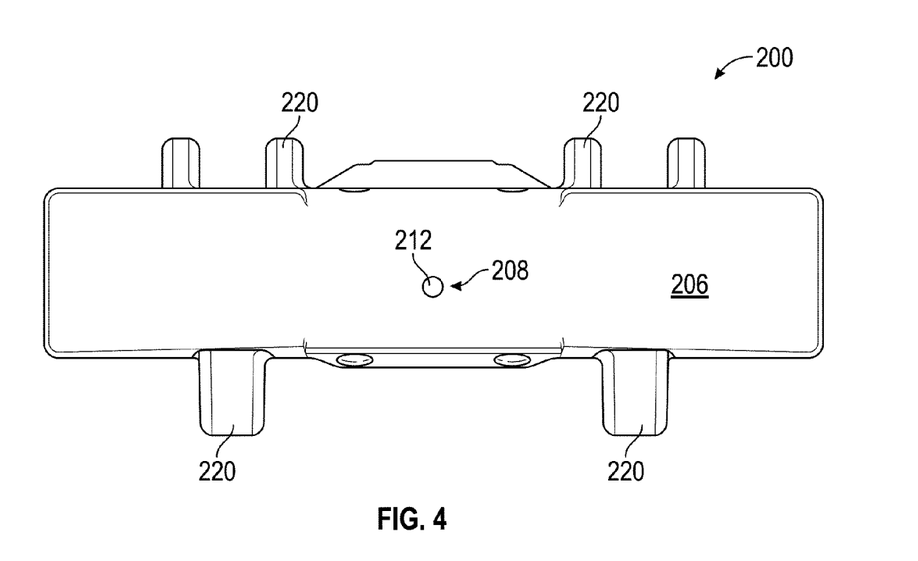
FIG. 4 is bottom view of the crawler shoe, according to an exemplary embodiment.

Referring now to FIGS. 2 through 4, the crawler shoe 200 is shown, according to an exemplary embodiment. The crawler shoe 200 includes pin lugs 220 configured to receive a pin in order to couple the pin lugs 220 to pin lugs of another crawler shoe. For instance, a plurality of crawler shoes 200 may be pivotally coupled via the pin lugs 220 in order to form the crawler track 102. The crawler shoe 200 also includes two drive lugs 202, which are formed on either side of a wear pad 224 (e.g., roller wear pad, track pad, cast crawler pad, etc.). As the crawler track 102 rotates about the side frame 108, the wear pad 224 is configured to interface (e.g., mate) with load rollers 110 of the undercarriage 106, absorbing a machine load (e.g., a force) from the load rollers 110. The drive lugs 202 include inside surfaces that are configured to interface with outer side surfaces of the load rollers 110 in order to guide the crawler track 102 between the drive lugs 202 and into contact with the wear pad 224 as the crawler track 102 rotates. The crawler shoe 200 also includes a core area 218 formed within the crawler shoe 200, including apertures formed at each end of the crawler shoe 200 which may extend along the length of the crawler shoe 200.

The crawler shoe 200 includes a plurality of wear surfaces (i.e., surfaces that are subject to abrasive and impact wear). In the illustrated embodiment, the crawler shoe 200 includes a first wear surface 206 and a second wear surface 204. In this embodiment, the first wear surface 206 is intended to contact the ground surface as the crawler track 102 is rotated to propel the vehicle 100. The second wear surface 204 is formed on the wear pad 224 and positioned opposite the first wear surface 206. In an exemplary embodiment, the wear pad 224 and/or the second wear surface 204 may be sized and/or shaped to receive or interface with the load rollers 110 of the undercarriage 106 as the crawler track 102 rotates around the side frame 108. In other embodiments, the surfaces 204 and 206 may be otherwise configured such that the second wear surface 204 faces outward on the crawler track 102 and the first wear surface 206 faces inward to interface with the load rollers 110 of the undercarriage 106. The first wear surface 206 also includes a recess 208 formed substantially within the first wear surface 206, and a measurement datum 212 formed at the bottom of the recess 208, which will be described in further detail in reference to FIG. 5.

The wear surfaces 206 and 204 are subject to wear during operation of the undercarriage 106. The wear surface 206 endures a significant portion of its wear from contact with the ground surface. As described above, the second wear surface 204 is configured to interface with the load rollers 110 of the undercarriage 106 as the crawler track 102 rotates around the side frame 108, absorbing a machine load or force from the load rollers 110. Thus, the second wear surface 204 may be subject to a significant amount of wear from the load rollers 110 and/or other components of the undercarriage 106 during operation of the vehicle 100. The surfaces 204 and 206 may also endure wear due to other conditions present on the vehicle 100 and/or within the work environment (e.g., debris, weather conditions, other abrasive and impact wear, etc.). As the wear surfaces 206 and 204 become worn, the crawler shoe 200 may require repair and/or replacement in order for the undercarriage 106 to operate efficiently.

Figure 5:
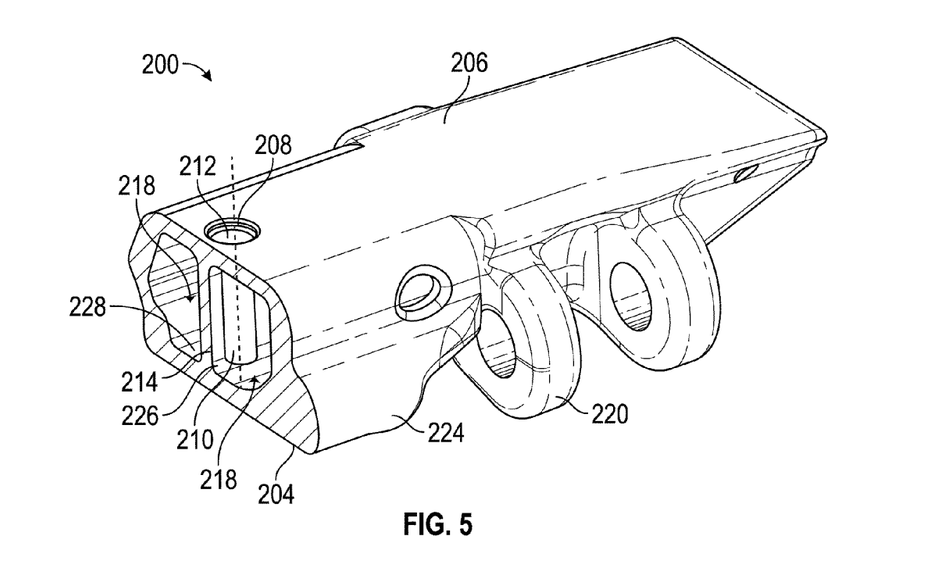
FIG. 5 is a cross-sectional perspective view of the crawler shoe along the 5-5 line of FIG. 3, according to an exemplary embodiment.

Referring now to FIG. 5, the crawler shoe 200 may also include an internal web 214 (e.g., support web) positioned between and approximately perpendicular to the wear surfaces 206 and 204. In the illustrated embodiment of FIG. 5, the internal web 214 is positioned within the core area 218 (e.g., surrounded by two apertures formed within the crawler shoe 200), extending from a position at or near the first wear surface 206 to a position at or near the second wear surface 204. The internal web 214 is intended to provide support for the crawler shoe 200 in response to compressive forces from the ground surface and the vehicle 100. The particular configuration of the internal web 214 may be determined based on the requirements of the internal web 214 and/or the crawler shoe 200. For instance, the width of the internal web 214 may be determined in order to sufficiently support forces applied to the crawler shoe 200, to appropriately size the core area 218 for a particular purpose, and/or for any other for another purpose related to the function of the internal web 214 and/or the crawler shoe 200.

The internal web 214 may also provide a material path for transmitting an ultrasonic signal through the crawler shoe 200, such as to determine a thickness of the crawler shoe 200 (e.g., a distance through the crawler shoe 200). In the illustrated embodiment, the crawler shoe 200 includes a transmission column 210 for transmission of an ultrasonic wave through the crawler shoe 200. As shown in FIG. 5, the transmission column 210 may be at least partially formed by the internal web 214 and may be used to obtain a wear measurement for the second wear surface 204. In other embodiments, such as in the illustrated embodiment of FIG. 6, the transmission column 210 may be formed through the crawler shoe 200 absent the internal web 214. The transmission column 210 may provide an approximately linear transmission path (shown by way of example as a dotted line in FIGS. 5 and 6) for transmitting an ultrasonic signal to the second wear surface 204, such as to obtain a wear measurement of the second wear surface 204. The transmission column 210 may be configured to provide the linear transmission path for the ultrasonic signal, such as by having a sufficient width to transmit the ultrasonic signal to the second wear surface 204.

Referring again to FIG. 5, the recess 208 is formed along the same axis as the transmission column 210. The recess 208 is configured to receive an ultrasonic probe 716. The probe 716 may be used as part of an ultrasonic measurement device 710 to determine a wear measurement of the crawler shoe 200. The device 710, including the probe 716, are shown in further detail in FIG. 7 and described more fully below. The recess 208 may be sized and/or shaped to receive the ultrasonic probe 716 (e.g., according to a configuration of the probe 716). In one embodiment, the recess 208 substantially matches one or more dimensions of the ultrasonic probe 716, such that the probe 716 fits uniformly within the recess 208. In another embodiment, the recess 208 has a shape that is larger than the size of the contact end of the ultrasonic probe 716. This may allow for limited movement of the ultrasonic probe 716 on measurement datum 212 to assure a proper connection of the ultrasonic signal. The shape of the recess 208 may also be configured to prevent larger debris from entering the recess 208 and causing wear on the measurement datum 212. The recess 208 is substantially round in the illustrated embodiment, but may be otherwise shaped in other embodiments according to the particular application of the crawler shoe 200, the recess 208, and/or the associated ultrasonic probe 716. The depth of the recess 208 (e.g., a distance from the wear surface 206 to the measurement datum 212) may be determined based on the amount of wear that is acceptable at the wear surface 206 prior to a wear-out condition of the wear pad 224 and/or replacement of the crawler shoe 200. For instance, the recess 208 may be sized and shaped such that the wear surface 206 and the measurement datum 212 may be approximately flush with one another when the wear pad 224 is at the wear-out condition and/or when the crawler shoe 200 requires replacement. The depth of the recess 208 may also be related to the associated ultrasonic probe (e.g., probe 716), such that the ultrasonic probe fits within the recess 208 to enable a measurement.

The measurement datum 212 is formed at a bottom portion of the recess 208. The measurement datum 212 provides a reference point for the measurement device 710 in order to determine a wear measurement (e.g., a thickness or width) of the crawler shoe 200. During use of the crawler track 102, the wear surfaces 206 and 204 and most other surfaces of the crawler shoe 200 may be subject to service wear from the ground surface (e.g., rock, sand, gravel, etc.), due to climatic conditions (e.g., precipitation, temperature deviation, wind, etc.), or from other components of the undercarriage 106. The measurement datum 212 is positioned at a bottom portion of the recess 208, such that the measurement datum 212 is less affected (e.g., minimally affected or worn) by regular service wear on the crawler shoe 200 (e.g., on the first wear surface 206). For instance, the measurement datum 212 may be positioned below the first wear surface 206 such that the measurement datum 212 receives less (e.g., minimal) service wear than the first wear surface 206. In an exemplary embodiment, the measurement datum 212 is positioned within the recess 208 such that the measurement datum 212 does not wear. In other embodiments, the measurement datum 212 is configured such that the measurement datum 212 receives only a negligible or inconsequential amount of wear relative to the first wear surface 206, but is not subjected to service wear. The placement of the measurement datum 212 on the crawler shoe 200 or within the recess 208 may be based on the configuration of the crawler shoe 200 and/or the conditions of the intended work environment. The initial depth of the measurement datum 212 relative to the associated wear surface (e.g., wear surface 206) may be based on the wear rate of the wear surface and/or the wear limit before replacement is required.

For instance, if the wear surface 206 receives a significant amount of wear before replacement, the measurement datum 212 may be placed at a greater depth relative to the wear surface 206. In an exemplary embodiment, the recess 208 is approximately fifty (50) millimeters in diameter and approximately fifteen (15) millimeters deep, such that the measurement datum 212 initially (e.g., prior to service wear) rests approximately fifteen millimeters below the first wear surface 206. The recess 208 and the measurement datum 212 may have a cast surface, or the recess 208 and/or the measurement datum 212 may be machined to improve the accuracy of measurements taken from the measurement datum 212.

Figure 6:
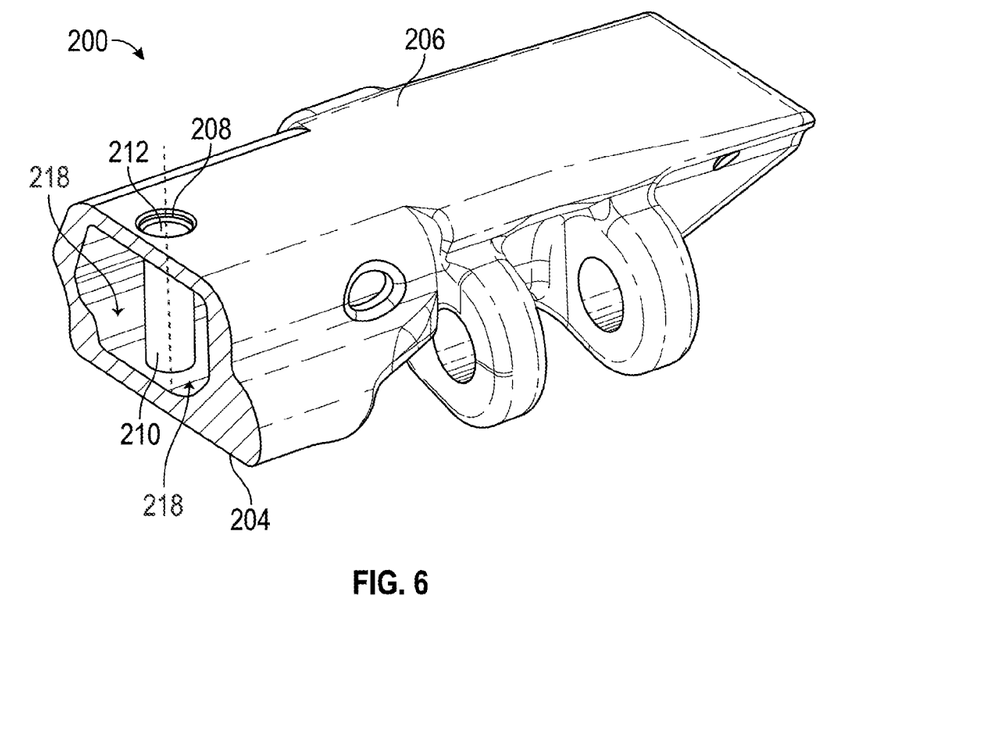
FIG. 6 is another cross-sectional view of the crawler shoe, according to another exemplary embodiment.

The measurement datum 212 may provide a contact point for the probe 716 in order to obtain a wear measurement through the transmission column 210. In an exemplary embodiment, the transmission column 210 provides an approximately linear transmission path for the ultrasonic signal from the measurement datum 212 to the second wear surface 204. The measurement datum 212 may form an endpoint of the transmission column 210 such that the probe 716 may contact the measurement datum 212 to transmit an ultrasonic wave through the transmission column 210. The measurement datum 212 may be a substantially flat surface (as shown in FIGS. 5 and 6), a pocket configured to receive the probe 716, or another type of reference configured to receive the probe 716. The measurement datum 212 may be substantially parallel to the first wear surface 206 and substantially perpendicular to the internal web 214 and/or the transmission column 210.

As shown in FIG. 5, the crawler shoe 200 also includes internal surfaces 226 and 228 that are positioned on the other side of the second wear surface 204. The internal surfaces 226 and 228 are substantially curved and uneven, such that a wear measurement of the second wear surface 204 using the surfaces 226 and 228 would produce an inaccurate measurement. As an example, the distance between the wear surface 204 and the internal surface 226 would vary according to the curvature of the internal surface 226 (i.e., according to the selected probe location). The transmission column 210, on the other hand, provides a reliable and consistent path for sending and receiving the ultrasonic signal. Likewise, the measurement datum 212 provides a non-wearing surface for consistent measurement of the distance between the measurement datum 212 and the target wear surface 204.

Referring now to FIG. 6, the transmission column 210 may be positioned between the wear surfaces 204 and 206 in order to provide additional support for the crawler shoe 200. In an exemplary embodiment, the transmission column 210 extends from the measurement datum 212 (e.g., the bottom of the recess 208) to the second wear surface 204. The transmission column 210 also provides a path for measurement via the ultrasonic probe 716. In one embodiment, the circular ends of the transmission column 210 are approximately thirty (30) millimeters in diameter.

In the illustrated embodiment of FIG. 6, the transmission column 210 is provided within the crawler shoe 200 absent the internal web 214. In this embodiment, the transmission column 210 may be provided within the core area 218 to support the forces applied by the ground surface and the mining vehicle 100. In an exemplary embodiment, the transmission column 210 is cylindrical in shape, having circular ends at the measurement datum 212 and the second wear surface 204. In other embodiments, such as the embodiment shown in FIG. 5, the transmission column 210 may also be integrated with the internal web 214. In these embodiments, the transmission column 210 may have a diameter greater than the thickness of the internal web 214.

Figure 7:
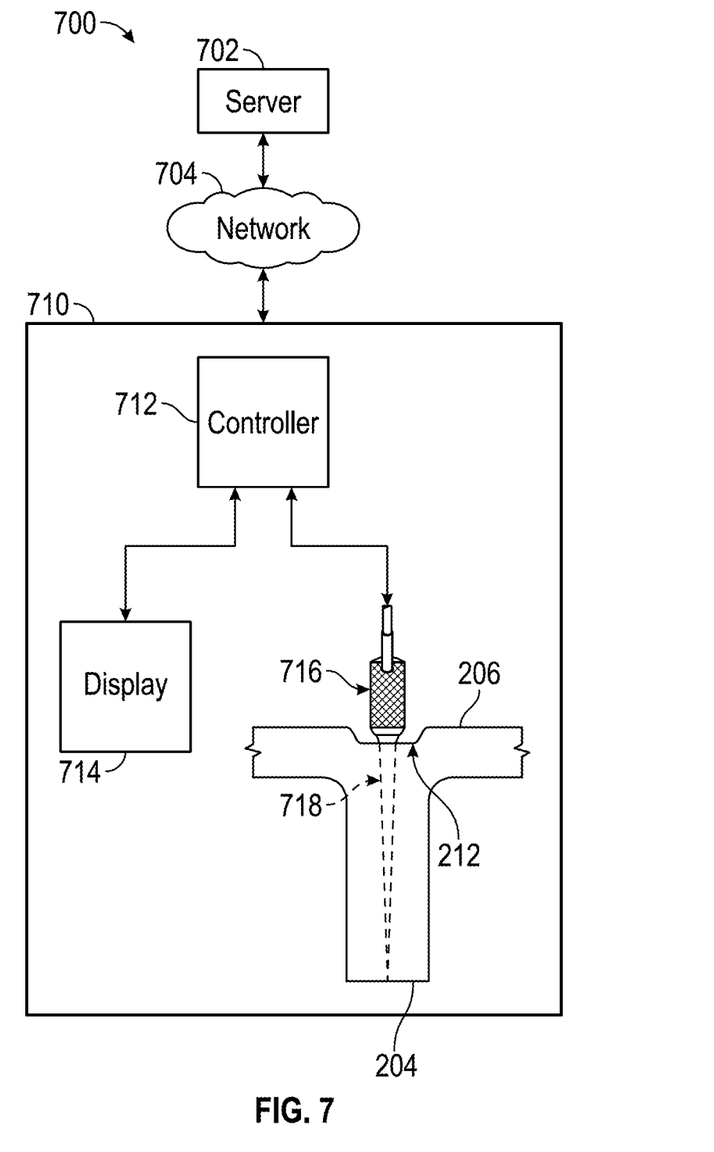
FIG. 7 is a block diagram of a system for measuring the cast crawler shoe, according to an exemplary embodiment.

Referring now to FIG. 7, an ultrasonic measurement system 700 is shown, according to an exemplary embodiment. The system 700 may be used to determine one or more dimensions of the crawler shoe 200 in order to determine wear of the crawler shoe 200. The system 700 will be described below in reference to measuring a distance between the measurement datum 212 and the second wear surface 204 (e.g., wear of the second wear surface 204), but the system 700 may be used to measure other components of the vehicle undercarriage 106 that are typically subject to wear, including links, bushings, load rollers 110, idlers, and sprockets. The system 700 may also be used to measure wear on other similar components for large industrial vehicles.

The system 700 includes an ultrasonic measurement device 710. The device 710 is configured to send an ultrasonic wave through the material of the crawler shoe 200 (e.g., through the transmission column 210) from a first surface (e.g., the measurement datum 212) and measure the amount of time before the wave is reflected from a second surface (e.g., the wear surface 204). The ultrasonic wave may be sent through an approximately linear transmission path. The device 710 may be configured to determine a measurement of the crawler shoe 200 based on the amount of time measured before the wave is reflected. For instance, the device 710 may be configured to compare the measurement with the original thickness of the crawler shoe 200 or a previous measurement in order to determine abrasive and impact wear (e.g., service wear) of the crawler shoe 200. The device 710 may also be configured to determine other information related to wear of the crawler shoe 200 based on the measurement, such as when the crawler shoe 200 or one of its components may require service or replacement.

As shown in FIG. 7, the device 710 includes an ultrasonic probe 716 for administering an ultrasonic signal such as wave 718. The probe 716 is configured to send the wave 718 through the crawler shoe 200 (e.g., at the measurement datum 212) and receive the wave 718 once it reflects from the second wear surface 204 of the crawler shoe 200. The probe 716 may be configured to measure various components of the mining vehicle 100. These various configurations of the ultrasonic probe 716 can be the signal frequency, or the diameter and shape of the probe contact surface, or the length of the probe 716.

The probe 716 is coupled to a controller 712 (i.e., control module) configured to control one or more operations of the measurement device 710. The controller 712 may be configured to receive and interpret electronic signals from the probe 716. In an exemplary embodiment, the probe 716 is configured to send a first electronic signal to the controller 712 when the wave 718 is sent (e.g., at the measurement datum 212) and a second electronic signal when the wave 718 is received (e.g., reflected from the second wear surface 204 of the crawler shoe 200). In this embodiment, the controller 712 is configured to determine (e.g., calculate) a thickness of the crawler shoe 200 based on the signals received from the probe 716 (e.g., an amount of time between when the signals are received). The controller 712 may also be configured to determine or calculate other information related to the crawler shoe 200 based on the signals, such as a wear measurement of the crawler shoe 200 or an estimated service interval for the crawler shoe 200. The controller 712 may include a processor configured to process data as part of the system 700, such as to process signals received from the probe 716. The controller 712 may also include a memory configured to store information received or calculated as part of the system 700.

In the illustrated embodiment, the controller 712 is coupled to a display 714. The display 714 may be an electronic display or screen configured to display information to a user of the device 710. For instance, the display 714 may be a viewable screen configured to display text to the user. In one embodiment, the display 714 is a touchscreen configured to receive inputs from the user and send signals to the controller 712 based on the inputs. In an exemplary embodiment, the controller 712 is configured to communicate with the display 714, including sending signals to the display 714 in order to cause the display 714 to display component information to the user, such as communications related to wear of the crawler shoe 200.

The system 700 may also include any number of servers and other devices, such as server 702 (e.g., remote storage device), which are configured to communicate with the measurement device 710 (e.g., controller 712) and support the various functions described herein. The various servers and other devices may be located at more than one physical location and configured to communicate remotely as part of the measurement system 700.

The measurement system 700 may further include a network 704 through which the measurement device 710 (e.g., controller 712) and the server 702 communicate. The network 704 may be any form of communications network that conveys data between the measurement device 710 and the server 702. The network 704 may include any number of wired or wireless connections, in various embodiments. In one embodiment, the server 702 is configured to communicate with the measurement device 710 over a wired connection that includes a serial cable, a fiber optic cable, a CAT5 cable, or another form of wired connection. For example, the device 710 may be connected to the server 702 (e.g., by the user) upon measuring the crawler shoe 200 in order to transmit the measurements to the server 702. In another example, the server 702 may communicate with the device 710 via a wireless connection (e.g., via WiFi, cellular, radio, etc.). The network 704 may also include any number of local area networks (LANs), wide area networks (WANs), or the Internet. Accordingly, the network 704 may include any number of intermediary networking devices, such as routers, switches, servers, etc.

In an exemplary embodiment, the measurement device 710 may be used to determine wear on the second wear surface 204 using the measurement datum 212. To obtain a wear measurement, the probe 716 is placed at the measurement datum 212 and an ultrasonic wave is generated and sent in the direction of the second wear surface 204. The ultrasonic wave is configured to reflect off of the second wear surface 204 and the probe 716 is configured to receive the reflected wave. The probe 716 may be configured to send a first signal to the controller 712 when the ultrasonic wave is sent and a second signal to the controller 712 when the reflected ultrasonic wave is received. Based on the signals, the controller 712 may determine a distance from the measurement datum 212 to the second wear surface 204, and thus determine a wear value or measurement of the second wear surface 204 relative to its original state or since the last measurement. In an exemplary embodiment, the measurement datum 212 is positioned at a depth such that it is subjected to minimal service wear. Thus, any reduction in the measured distance from the measurement datum 212 to the second wear surface 204 may be attributed to wear of the second wear surface 204. The controller 712 may be configured to determine whether replacement of the crawler shoe 200 is required based on wear of the second wear surface 204.

The measurement system 700 may also include a depth gauge 230 (shown more particularly in FIG. 9) configured to measure a surface of the crawler shoe 200 adjacent to the measurement datum 212. In an exemplary embodiment, the depth gauge 230 may be placed on top of the first wear surface 206 in order to measure wear of the first wear surface 206. The depth gauge 230 may include an adjustable depth probe 232 that may be positioned within the recess 208 such that the depth probe 232 contacts the measurement datum 212 in order to determine a wear measurement of the first wear surface 206.

In other embodiments, the recess 208 may be formed within another surface of the crawler shoe 200 in order to measure the wear on an opposite surface of the crawler shoe 200. In one embodiment, for instance, the recess 208 and the measurement datum 212 are formed on the second wear surface 204 in order to obtain a wear measurement of the first wear surface 206. In another embodiment, the crawler shoe 200 includes a second recess and a second measurement datum formed within the second wear surface 204. In this embodiment, the second recess and the second measurement datum are substantially similar to the first recess 208 and the first measurement datum 212, respectively. The second recess and the second measurement datum may be used to determine a wear measurement of the first wear surface 206. Further in this embodiment, the transmission column 210 and/or the internal web 214 may provide an approximately linear second transmission path for the ultrasonic signal (e.g., wave 718). The second transmission path may extend from the second measurement datum to the first wear surface 206 (e.g., through the transmission column 210). The second transmission path may be provided in order to determine a wear measurement of the first wear surface 206.

Figure 8:
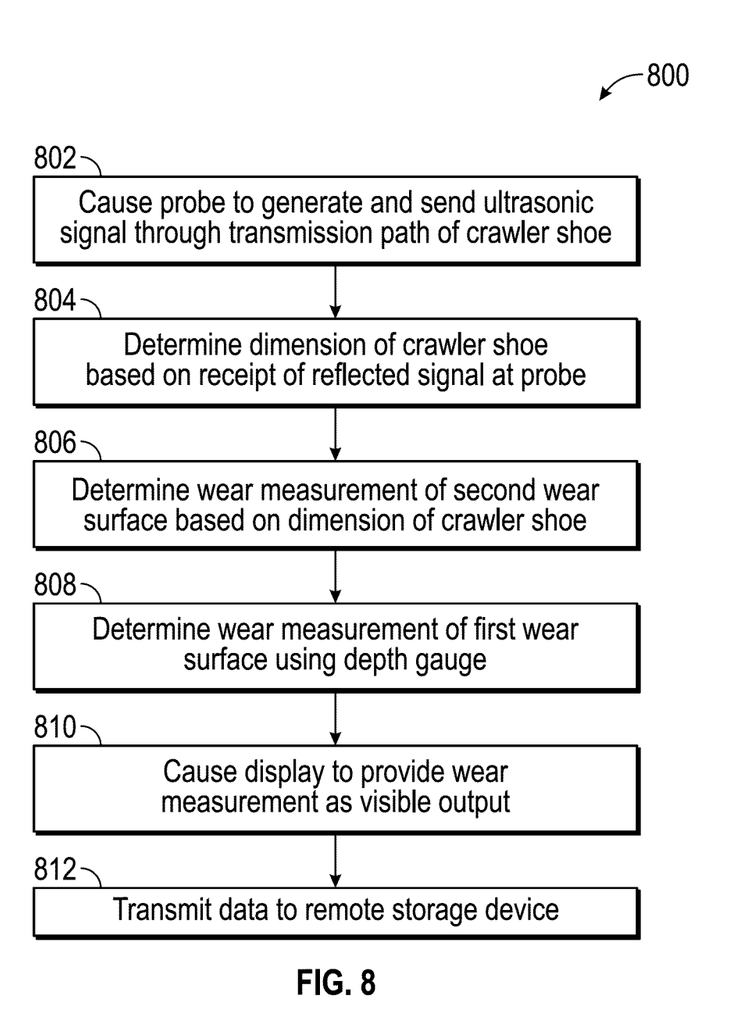
FIG. 8 is a flow chart diagram of a method for determining a wear measurement of a crawler shoe, according to an exemplary embodiment.

Referring now to FIG. 8, a process 800 for determining wear of a crawler shoe 200 is shown, according to an exemplary embodiment. Although the process 800 is described in reference to the crawler shoe 200, the process 800 may also be used to measure wear of another component of the vehicle 100 or another large industrial vehicle. In an exemplary embodiment, the process 800 is executed by the controller 712. The controller 712 may include a processor configured to execute stored instructions and a memory configured to store the instructions as well as measurements obtained via the process 800. The process 800 may also be executed, in whole or in part, by the server 702 or another processing circuit. Likewise, the process 800 may be executed at the measurement device 710 or remotely (e.g., at server 702).

At 802, a signal is sent to the probe 716 (e.g., by the controller 712), causing the probe 716 to generate and send an ultrasonic wave. The probe 716 is intended to send the wave through the transmission column 210 of the crawler shoe 200 (i.e., in the direction of the second wear surface 204) such that the wave is reflected off of the second wear surface 204. The probe 716 may be positioned to contact the measurement datum 212 when the ultrasonic wave is generated and/or sent. In an exemplary embodiment, the transmission column 210 extends to the second wear surface 204, such that the ultrasonic wave is reflected from the second wear surface 204. The reflected wave is received at the probe 716. The probe 716 may be configured to automatically send a first signal to the controller 712 when the ultrasonic wave is sent, and to automatically send a second signal to the controller 712 when the ultrasonic wave is received (e.g., reflected from the second wear surface 204 and received at the probe 716).

At 804, a measurement (e.g., a dimension) of the crawler shoe 200 is determined based on receipt of the reflected wave at the probe 716 (e.g., based on the first and second signals). The dimension may be determined by the controller 712 immediately upon receipt of the second signal (i.e., upon receipt of the reflected wave at the probe 716). In an exemplary embodiment, the controller 712 determines a thickness of the crawler shoe 200 from the measurement datum 212 to the second wear surface 204 based on receipt of the reflected wave at the probe 716 (e.g., based on the first and second signals). For instance, the controller 712 may determine the thickness of the crawler shoe 200 through the transmission column 210 based on the duration of time between when the first signal is received and when the second signal is received (i.e., duration of time between when the wave is sent and when the reflected wave is received). The controller 712 may also be configured to determine the thickness of the crawler shoe 200 based on the type of material comprising the crawler shoe 200 and any other information received as part of the system 700.

At 806, a wear measurement for the crawler shoe 200 (e.g., the second wear surface 204) is determined based on the dimension of the crawler shoe 200 (e.g., the thickness through the transmission column 210). For instance, the wear measurement may be an amount that the second wear surface 204 has been worn relative to an original dimension or a previous measurement. The wear measurement may be determined by comparing the determined dimension of the crawler shoe 200 to stored data for the crawler shoe 200. For instance, crawler shoe data may be stored within memory of the controller 712 and the controller 712 may be configured to compare the determined dimension to a previous dimension of the crawler shoe 200 in order to determine the wear measurement.

Figure 9:
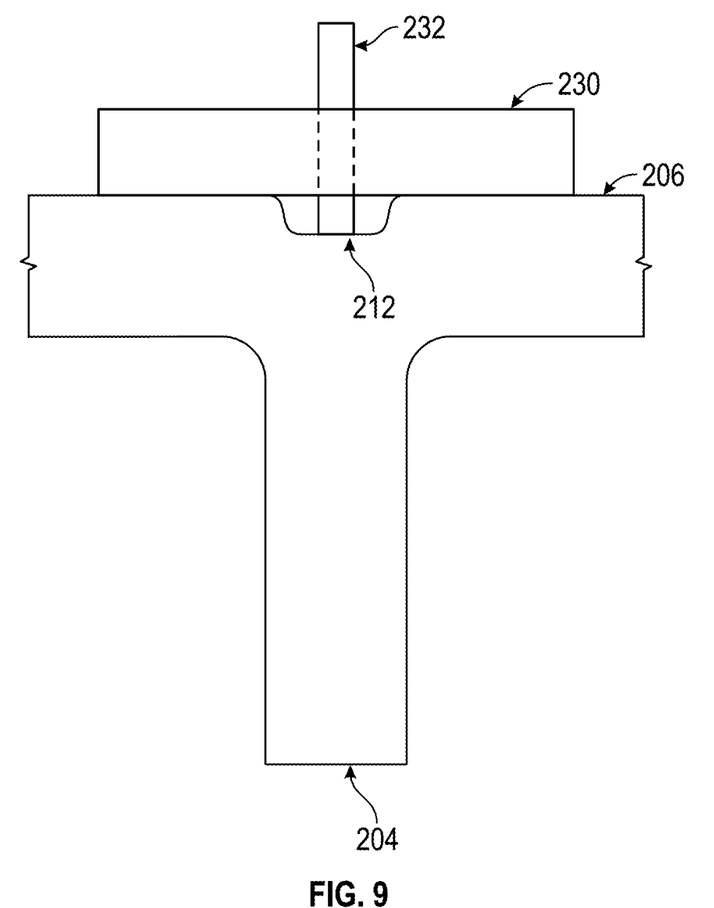
FIG. 9 is a cross-sectional diagram view of the crawler shoe and a mechanical depth gauge, according to an exemplary embodiment.

At 808, a wear measurement for the first wear surface 206 may be determined using a depth gauge 230. The depth gauge 230 may be placed in contact with the first wear surface 206. The adjustable depth probe 232 is positioned to contact the measurement datum 212 in order to determine a distance between the measurement datum 212 and the first wear surface 206. The distance may be used to determine a wear measurement for the first wear surface 206. For instance, the measured distance may be compared to a wear table, or to a previous measurement for the first wear surface 206 in order to determine the wear measurement. The wear measurements may be used to determine whether a wear-out condition of the first wear surface 206 or whether to replace or repair the crawler shoe 200.

At 810, a display (e.g., display 714) of the measurement device 710 may be caused to provide the wear measurement as a visible output. For instance, the display 714 may be a screen configured to display text to a user of the device 710. The display 714 may be coupled to the controller 712. At 812, data related to the crawler shoe 200 (e.g., the wear measurement) may be transmitted to a remote storage device (e.g., server 702), including any data or information measured, determined, or calculated as part of the process 800. The data may be transmitted via the network 704 or another network configured to transmit data remotely.

The construction and arrangement of the crawler shoe, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

INDUSTRIAL APPLICABILITY

The disclosed crawler shoe 200 may be implemented on any track-driven vehicle (e.g., vehicle 100) having a track (e.g., crawler track 102) comprised of a plurality of crawler shoes. The disclosed crawler shoe 200 may be implemented to enable more accurate measurement of service wear on the crawler shoe 200 in order to better determine when replacement or repair is required. The disclosed crawler shoe 200 may also reduce the time required to measure service wear on the crawler shoe 200 by providing the measurement datum 212 conveniently located to enable an efficient and accurate measurement of a wear surface (e.g., wear surface 204) of the crawler shoe 200.

It will be apparent to those skilled in the art that various modifications and variations can be made to the disclosed crawler shoe having wear measurement features. Other embodiments will be apparent to those skilled in the art from consideration of the specification and practice of the disclosed crawler shoe having wear measurement features. It is intended that the specification and examples be considered as exemplary only, with a true scope being indicated by the following claims and their equivalents.

What is claimed is:

1. A crawler shoe for a mining vehicle, the crawler shoe comprising:
    a first wear surface;
    a second wear surface positioned opposite the first wear surface;
    a recess formed within the first wear surface and including a measurement datum formed at a bottom portion of the recess, wherein the measurement datum is positioned below the first wear surface such that the measurement datum is subjected to less service wear than the first wear surface; and
    an approximately linear transmission path configured to receive an ultrasonic signal and extending from the measurement datum to the second wear surface.

2. The crawler shoe of claim 1, further comprising:
    a transmission column positioned between and approximately perpendicular to the first and second wear surfaces, wherein the transmission path extends through the transmission column, and wherein the transmission path is provided for determining a wear measurement of the second wear surface.

3. The crawler shoe of claim 2, further comprising:
    a core area extending from a first end of the crawler shoe to a second end of the crawler shoe; and
    an internal web formed within the core area and positioned between the first and second wear surfaces, wherein the internal web is integrated with the transmission column and extends out from the transmission column toward the first and second ends of the crawler shoe, and wherein the internal web is configured to provide additional support for the first and second wear surfaces.

4. The crawler shoe of claim 2, further comprising:
    a second recess formed within the second wear surface and including a second measurement datum formed at a bottom portion of the second recess, wherein the second measurement datum is positioned below the second wear surface such that the second measurement datum is subjected to less service wear than the second wear surface; and
    an approximately linear second transmission path configured to receive the ultrasonic signal and extending from the second measurement datum to the first wear surface through the transmission column, wherein the second transmission path is provided for determining a wear measurement of the first wear surface.

5. The crawler shoe of claim 1, wherein the measurement datum is configured to receive less service wear than the first wear surface.

6. The crawler shoe of claim 1, wherein the recess is configured to receive a probe of a measurement device, and wherein the measurement datum provides a contact surface for locating the probe in order to send the ultrasonic signal through the transmission path and determine a wear measurement for the second wear surface.

7. An undercarriage system, the system comprising:
    a load roller; and
    a track comprising a plurality of interconnected crawler shoes configured to engage the load roller, wherein each of the crawler shoes is pivotably coupled to adjacent crawler shoes by a pin, and wherein at least one of the crawler shoes comprises:
        a first wear surface;
        a second wear surface positioned opposite the first wear surface, wherein the second wear surface is configured to engage the load roller;
        a recess formed within the first wear surface and having a measurement datum formed at a bottom portion of the recess, wherein the measurement datum is positioned below the first wear surface such that the measurement datum is subjected to less service wear than the first wear surface; and
        an approximately linear transmission path configured to receive an ultrasonic signal and extending from the measurement datum to the second wear surface.

8. The system of claim 7, wherein the at least one crawler shoes further comprises:
    a transmission column positioned between and approximately perpendicular to the first and second wear surfaces, wherein the transmission path extends through the transmission column, and wherein the transmission path is provided for determining a wear measurement of the second wear surface.

9. The system of claim 8, wherein the at least one crawler shoes further comprises:
    a core area extending from a first end of the at least one crawler shoes to a second end of the at least one crawler shoes; and
    an internal web formed within the core area and positioned between the first and second wear surfaces, wherein the internal web is integrated with the transmission column and extends out from the transmission column toward the first and second ends of the at least one crawler shoes, and wherein the internal web is configured to provide additional support for the first and second wear surfaces.

10. The system of claim 7, wherein the recess is configured to receive an ultrasonic probe, and wherein the measurement datum provides a contact surface for locating the ultrasonic probe in order to determine a wear measurement of the second wear surface.

11. The system of claim 10, wherein the measurement datum is substantially flat and positioned approximately parallel to the second wear surface, and wherein the recess is configured to receive the ultrasonic probe such that the ultrasonic probe rests substantially flat against the contact surface.

12. The system of claim 7, wherein the at least one crawler shoes further comprises:
   a second recess formed within the second wear surface and including a second measurement datum formed at a bottom portion of the second recess, wherein the second measurement datum is positioned below the second wear surface such that the second measurement datum is subjected to less service wear than the second wear surface; and
   an approximately linear second transmission path configured to receive the ultrasonic signal and extending from the second measurement datum to the first wear surface, wherein the second transmission path is provided for determining a wear measurement of the first wear surface.

13. The system of claim 7, wherein the measurement datum is configured to receive less service wear than the first wear surface.

14. The system of claim 7, further comprising:
   a controller configured to receive electronic signals from an ultrasonic measurement device configured to generate the ultrasonic signal, wherein the controller comprises a processor configured to determine the wear measurement of the second wear surface based on the electronic signals.

15. A computer-implemented method for determining wear of a crawler shoe, the method comprising:
   causing a probe of a measurement device to generate and send an ultrasonic signal through an approximately linear transmission path of a crawler shoe, wherein the crawler shoe includes:
      a first wear surface;
      a second wear surface positioned opposite the first wear surface and configured to reflect the ultrasonic signal; and
      a recess formed within the first wear surface and including a measurement datum formed at a bottom portion of the recess, wherein the measurement datum is positioned below the first wear surface such that the measurement datum is subjected to less service wear than the first wear surface, wherein the transmission path extends from the measurement datum to the second wear surface; and
   determining a wear measurement of the second wear surface based upon receipt of the ultrasonic signal at the probe.

16. The method of claim 15, wherein the probe is configured to generate a first electronic signal when the ultrasonic signal is sent, and to generate a second electronic signal when the ultrasonic signal is received, and wherein the wear measurement is determined based on the first and second electronic signals.

17. The method of claim 15, further comprising:
   transmitting data to a remote storage device for storing the data;
   wherein the data includes the wear measurement.

18. The method of claim 15, further comprising:
   determining a distance between the measurement datum and the second wear surface based on receipt of the ultrasonic signal at the probe;
   wherein the wear measurement of the second wear surface is determined based on the distance between the measurement datum and the second wear surface.

19. The method of claim 15, further comprising:
   causing a display of the measurement device to provide the wear measurement as a visible output.

20. The method of claim 15, further comprising:
   using a depth gauge, determining a distance between the measurement datum and the first wear surface; and
   determining a wear measurement of the first wear surface based on the distance between the measurement datum and the first wear surface.

\* \* \* \* \*